United States Patent
Chang et al.

(10) Patent No.: US 12,290,548 B2
(45) Date of Patent: May 6, 2025

(54) HERBAL COMPOSITION FOR REDUCING URIC ACID AND THE USE IN REDUCING URIC ACID, BODY FAT, AND BLOOD GLUCOSE THEREOF

(71) Applicant: LYTONE ENTERPRISE, INC., New Taipei (TW)

(72) Inventors: William Tien-hung Chang, New Taipei (TW); Wei-ting Chang, New Taipei (TW)

(73) Assignee: LYTONE ENTERPRISE, INC., New Taipei (TW)

( * ) Notice: Subject to any disclaimer, the term of this patent is extended or adjusted under 35 U.S.C. 154(b) by 0 days.

(21) Appl. No.: 17/349,061

(22) Filed: Jun. 16, 2021

(65) Prior Publication Data
US 2021/0393730 A1    Dec. 23, 2021

(30) Foreign Application Priority Data
Jun. 17, 2020   (TW) .................. 109120486

(51) Int. Cl.
| | |
|---|---|
| *A61K 36/79* | (2006.01) |
| *A61K 36/064* | (2006.01) |
| *A61K 36/42* | (2006.01) |
| *A61K 36/605* | (2006.01) |
| *A61K 36/61* | (2006.01) |
| *A61K 36/82* | (2006.01) |

(Continued)

(52) U.S. Cl.
CPC ........ *A61K 36/8998* (2013.01); *A61K 36/064* (2013.01); *A61K 36/42* (2013.01); *A61K 36/605* (2013.01); *A61K 36/61* (2013.01); *A61K 36/79* (2013.01); *A61K 36/82* (2013.01); *A61K 36/87* (2013.01); *A61P 3/04* (2018.01)

(58) Field of Classification Search
CPC .... A61K 36/79; A61K 36/61; A61K 36/8998; A61K 36/064; A61K 36/42; A61K 36/605; A61K 36/82; A61K 36/87; A61P 3/04

See application file for complete search history.

(56) References Cited

U.S. PATENT DOCUMENTS

| | | | |
|---|---|---|---|
| 8,017,147 B2 * | 9/2011 | Mazed | A61K 36/45 977/773 |
| 2011/0213026 A1 | 9/2011 | Grothe et al. | |
| 2019/0038576 A1 | 2/2019 | Baron et al. | |

FOREIGN PATENT DOCUMENTS

| | | | |
|---|---|---|---|
| CN | 104116990 A | * | 10/2014 |
| CN | 104161881 A | | 11/2014 |

(Continued)

OTHER PUBLICATIONS

Liu et al., Mesenteric Fat Thickness is an Independent Determinant of Metabolic Syndrome and Identifies Subjects With Increased Carotid Intima-Media Thickness, 2006, Diabetes Care 29:379-384 (Year: 2006).*

(Continued)

*Primary Examiner* — David W Berke-Schlessel
*Assistant Examiner* — Trent R Clarke
(74) *Attorney, Agent, or Firm* — Birch, Stewart, Kolasch & Birch, LLP

(57) ABSTRACT

Provided herein is a pharmaceutical composition comprising 1-2 part by weight of *Schisandra chinensis* powder and 5-10 part by weight of extract of *Psidium guajava* L. The composition can be used in the treatment of reducing blood uric acid, protecting pancreatic beta cell, and reducing body fat.

5 Claims, 11 Drawing Sheets

(51) Int. Cl.
*A61K 36/87* (2006.01)
*A61K 36/8998* (2006.01)
*A61P 3/04* (2006.01)

(56) References Cited

FOREIGN PATENT DOCUMENTS

| CN | 104815140 A | * | 8/2015 |
|---|---|---|---|
| CN | 104873624 A | | 9/2015 |
| CN | 105707863 A | * | 6/2016 |
| CN | 106310000 A | | 1/2017 |
| CN | 108524814 A | * | 9/2018 |
| CN | 109395028 A | | 3/2019 |
| JP | 5-238943 A | | 9/1993 |
| JP | 2002-370980 A | | 12/2002 |
| KR | 10-2010-0035081 A | | 4/2010 |
| TW | 201429486 A | | 8/2011 |
| WO | WO 2009/093584 A1 | | 7/2009 |
| WO | WO 2019/239215 A2 | | 12/2019 |

OTHER PUBLICATIONS

Chinese Office Action and Search Report for Chinese Application No. 202110667236.0, dated Sep. 19, 2023, with an English translation of the Search Report.
Extended European Search Report for European Application No. 21179705.5, dated Sep. 17, 2021.
Ghalehkandi et al., "Effect of Garlic (*Allium sativum*) Aqueous Extract on serum values of Urea, Uric-Acid and Creatinine compared with Chromium Chloride in Male Rats," Annals of Biological Research, vol. 3, No. 9, 2012, pp. 4485-4490.
Irondi et al., "Guava leaves polyphenolics-rich extract inhibits vital enzymes implicated in gout and hypertension in vitro," Journal of Intercultural Ethnopharmacology, vol. 5, No. 2, 2016, pp. 122-130.
Japanese Office Action for Japanese Application No. 2021-100483, dated Dec. 3, 2024, with an English translation.
Wang et al., "Administration of Procyanidins from Grape Seeds Reduces Serum Uric Acid Levels and Decreases Hepatic Xanthine Dehydrogenase/Oxidase Activities in Oxonate-Treated Mice," Basic & Clinical Pharmacology & Toxicology, vol. 94, 2004, pp. 232-237.

* cited by examiner

HERBAL COMPOSITION FOR REDUCING URIC ACID AND THE USE IN REDUCING URIC ACID, BODY FAT, AND BLOOD GLUCOSE THEREOF

FIELD OF THE INVENTION

The present disclosure is related to a pharmaceutical composition which can reduce blood uric acid, protect pancreatic beta cell, and reduce body fat.

BACKGROUND OF THE INVENTION

Hyperuricemia is defined as that the blood uric acid concentration is higher than 6.8-7.0 mg/dL for a male subject or is higher than 6.0 mg/dL for a female subject. Hyperuricemia and its related metabolic diseases (e.g. gout) affect the health condition in US for 3-5 million people. The incidence rate of hyperuricemia would increase as the prolonging of average lifetime, change of food habit, intake of alcohol, and the conditions related to high uric acid (e.g. metabolic syndromes, renal dysfunction, or hypertension). There are some additional factors that would affect the incidence of hyperuricemia, including age and ethnics.

Diabetes mellitus refers to the disease resulted from the progression of multiple factors. The typical symptoms include the elevation of blood sugar, i.e. hyperglycemia. According to the report of American Diabetes Society, approximately 6% of the global population are suffered from diabetes. The patient's inability to control the high blood sugar level leads to increased mortality, as well as cardiovascular disease, renal disease, neurological disease, eye disease, hypertension, or cerebrovascular disease. Thus, the control of homeostasis is the key of the treatment of diabetes.

Dyslipidemia refers to the disease having abnormal concentration of blood lipoprotein, which often concurs with diabetes and is a crucial cause of cardiovascular disease and mortality of diabetic subject. It was reported that the death rate caused by coronary artery disease of diabetic subject is several times higher than that of non-diabetic subject.

Hyperuricemia, diabetes and dyslipidemia are often present in people with metabolic disorders, which is the so-called metabolic syndrome. In view of the prevalence of the above-mentioned diseases, there is a need to develop a therapeutic agent which can improve the homeostasis of blood. The present invention aims to treat patients having metabolic syndrome with a single formulation which is able to safely and effectively alleviate various symptoms and avoid potential side effects of western medicines.

SUMMARY OF THE INVENTION

An aspect provided herein is a method of reducing blood uric acid, comprising administering to a subject in need a therapeutic effective amount of a pharmaceutical composition comprising: 1-2 part by weight of extract of *Schisandra chinensis* and 5-10 part by weight of extract of *Psidium guajava*.

In a particular embodiment, the pharmaceutical composition comprises 1 part by weight of *Schisandra chinensis* and 5 part by weight of extract of *Psidium guajava*.

In a particular embodiment, the pharmaceutical composition further comprises 2-3 part by weight of extract of *Hordeum vulgare*.

In a particular embodiment, the pharmaceutical composition further comprises active ingredient select from the group consisting of: 2-3 part by weight of extract of *Hordeum vulgare*, 8-10 part by weight of extract of *Morus alba*, 5-10 part by weight of extract of *Camellia sinensis*, 5-10 part by weight of extract of grape seed, 2-3 part by weight of Chromium yeast, 3-5 part by weight of powder of Momordicae sharantia, and the combination of at least one of the aforementioned ingredient.

In a particular embodiment, the method is to maintain the normal renal function.

In a particular embodiment, the method is to inhibit the activity of xanthine oxidase.

Another aspect provided herein is a method of protecting pancreatic β cell, comprising administering to a subject in need a therapeutic effective amount of the pharmaceutical composition.

In a particular embodiment, the method is to maintain the weight of β cell of a diabetic subject.

In a particular embodiment, the method is the treatment of insulin resistance.

Another aspect provided herein is a method of reducing body fat, comprising administering to a subject in need a therapeutic effective amount of the pharmaceutical composition.

In a particular embodiment, the method is to lower the fat of organ and body weight, and to increase the ratio of body muscle.

In a particular embodiment, the method is a treatment of dyslipidemia.

BRIEF DESCRIPTION OF THE DRAWINGS

The features of the disclosure are set forth with particularity in the appended claims. A better understanding of the features and advantages of the present invention will be obtained by reference to the following detailed description that sets forth illustrative embodiments, in which the principles of the disclosure are utilized, and the accompanying drawings of which:

DESCRIPTION OF THE INVENTION

Figure 1:
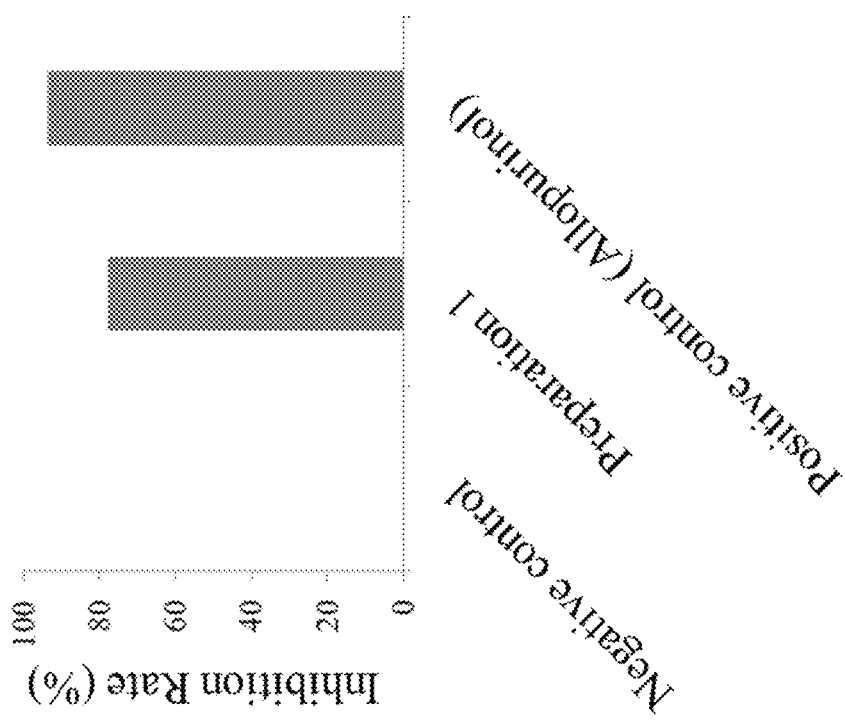
FIG. 1 shows the illustrative result of the inhibition of activity of xanthine oxidase (XO) by the composition according to the present disclosure, including a negative control group (without treatment), the group treated with the composition according to the present disclosure, and a positive control group treated with Allopurinol.

The following embodiments when read with the accompanying drawings are made to clearly exhibit the above-mentioned and other technical contents, features and effects of the present disclosure. Through the description by means of the embodiments, a person of ordinary skills in the art would explicitly understand the technical approach and effects the present disclosure adopts to achieve the above-identified aspect.

Unless otherwise defined, all the technical and scientific terms used herein have the same definition as commonly understood by a person of ordinary skills in the art to which the present disclosure pertains.

As used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described. Unless otherwise specified, all the material used herein is commercial and can be easily obtained.

The term "about" used herein refers to a measured quantity, such as dose, including the deviation ±15% or ±10% relative to a specified quantity in an embodiment; the deviation ±5% relative to a specified quantity in a preferred embodiment; the deviation ±1% relative to a specified quantity in a further preferred embodiment; or the deviation ±0.1% relative to a specified quantity in a most preferred embodiment; whereas the nature of the substance the quantity pertains to is not affected thereby.

High blood uric acid, also known as hyperuricemia, refers to the abnormal elevation of concentration of blood uric acid.

Specifically, hyperuricemia refers to a long-term excessive concentration of blood uric acid of a subject. The possible cause of hyperuricemia is the overproduction of uric acid or the low excretion of uric acid. The etiological cause of hyperuricemia includes obesity, excessive intake of alcohol or purine, use of medicine (e.g. chemotherapy drugs or immunosuppressors), hypertension, diseases related to hemoglobin, haemolytic anemia, sickle cell anemia, renal disorders, myeloproliferative disease, lymphoproliferative diseases, hyperparathyroidism, diseases related to insulin resistance, diabetes mellitus, transplant of organ, or genetic defect of enzyme.

The term "diabetes mellitus" (diabetes) used herein includes type I diabetes, type II diabetes, gestational diabetes or other conditions having typical symptoms of diabetes.

The term "diabetes mellitus" (diabetes) used herein refers to the metabolic disorder relative to the malfunction of the production or the consumption of glucose, such that the concentration of blood glucose cannot be controlled at a normal level.

High blood fat, also known as hyperlipidemia, refers to the abnormality of concentration of lipoprotein, e.g. high VLDL and low HDL.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutically acceptable" as used herein refers to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

The term "carrier" used herein refers to the nontoxic compound or pharmaceuticals which assist cells or tissue to absorb medicine, including solid, liquid, or semi-liquid carriers.

The pharmaceutically acceptable carrier(s) can be selected from, for example, excipients, adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions.

Examples of suitable excipient include but are not limited to lactose, glucose, sucrose, sorbitol, mannose, starch, arabia gum, calcium phosphate, alginate, tragacanth gum, gelatin, calcium silicate, microcrystalline cellulose, polyvinylpyrrolidone (PVP), cellulose, ddH$_2$O, syrup, or methylcellulose.

According to the present disclosure, the pharmaceutical compositions can be in any form suitable for oral, parenteral, topical, intranasal, intrabronchial, sublingual, rectal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules (hard or soft shell), caplets, pills, lozenges, syrups, solutions, powders, granules, elixirs, suspensions, sublingual tablets, wafers, or patches such as buccal patches.

The pharmaceutical composition as disclosed herein can be preserved by lyophilization and can be reconstituted with a suitable carrier before use. The lyophilization and reconstruction can be performed according to the ordinary skills in the art and a skilled person would appreciate that lyophilization and reconstruction contribute to a certain degree of loss of activity and the dose of pharmaceutical should be adjusted upwards for compensation.

The pharmaceutical composition as disclosed herein can be combined with other therapeutic agent for reducing blood uric acid, as a combination therapy. The therapeutic agent for reducing blood uric acid is selected from at least one of allopurinol, febuxostat, sulphinpyrazone, benzbromarone, probenecid, pegloticase, puricase, rasburicase, pegylated uricase, fenofibrate.

One aspect provided herein is to provide a pharmaceutical composition comprising: 1-2 part by weight of extract of *Schisandra chinensis* and 5-10 part by weight of extract of *Psidium guajava*.

The pharmaceutical composition as disclosed herein can further comprise a pharmaceutically acceptable carrier.

In a particular embodiment, the pharmaceutical composition further comprises active ingredient select from the group consisting of: 2-3 part by weight of extract of *Hordeum vulgare*, 8-10 part by weight of extract of *Morus alba*, 5-10 part by weight of extract of *Camellia sinensis*, 5-10 part by weight of extract of grape seed, 2-3 part by weight of Chromium yeast, 3-5 part by weight of powder of Momordicae sharantia, and the combination of at least one of the aforementioned ingredient.

In a particular embodiment, the pharmaceutical composition comprises 1 part by weight of *Schisandra chinensis* and 5 part by weight of extract of *Psidium guajava*.

In a particular embodiment, the pharmaceutical composition comprises about 1 part by weight of extract of *Schisandra chinensis*, about 5 part by weight of extract of *Psidium guajava*, and about 3 part by weight of extract of *Hordeum vulgare*.

In a particular embodiment, the pharmaceutical composition comprises about 1 part by weight of extract of *Schisandra chinensis*, about 5 part by weight of extract of *Psidium guajava*, about 3 part by weight of extract of *Hordeum vulgare*, about 10 part by weight of extract of Moms alba, about 10 part by weight of extract of *Camellia sinensis*, about 10 part by weight of extract of grape seed, about 3 part by weight of Chromium yeast, and about 5 part by weight of powder of Momordicae sharantia.

In a particular embodiment, the aforementioned extracts are administered separately or simultaneously.

In a particular embodiment, the pharmaceutical composition as disclosed herein is administered orally or parenterally.

An aspect disclosed herein is to provide a method for treatment of the diseases or conditions related to high blood uric acid, comprising administering to a subject in need a therapeutic effective amount of a pharmaceutical composition as disclosed herein.

Another aspect disclosed herein is to provide a pharmaceutical composition for manufacturing the medicament for the diseases or conditions related to high blood uric acid.

In a particular embodiment, the medicament is used in maintaining the normal renal function.

In a particular embodiment, the medicament is used in inhibiting the activity of xanthine oxidase.

According to the present disclosure, the medicament is used in the prevention or treatment of renal disease, gout, obesity, diabetes mellitus, insulin resistance, or metabolic syndrome.

According to the present disclosure, the medicament is predictably used in the prevention or treatment of the diseases or conditions related to high blood uric acid, including but not limited to: hyperlipidemia, non-alcoholic fatty liver disease (NAFLD), non-alcoholic steatohepatitis (NASH), atherosclerosis, or hypertension.

In a particular, the medicament is used in the treatment of gout or renal disease (including acute nephropathy, chronic nephropathy, uric nephrolithiasis, or chronic renal diseases).

Another aspect of the present disclosure is to provide a use of the pharmaceutical composition as disclosed herein for manufacturing the medicament for protecting pancreatic β cells.

In a particular embodiment, the medicament is used in maintaining the weight of β cells of a diabetic subject.

In a particular embodiment, the medicament is used in the treatment of insulin resistance.

Another aspect of the present disclosure is to provide a use of the pharmaceutical composition as disclosed herein for manufacturing the medicament for reducing body fat.

In a particular embodiment, the medicament is used in lowering the fat of organ and body weight, and to increase the ratio of body muscle.

Preparation

The pharmaceutical composition used in the present disclosure comprises 1-2 part by weight of extract of *Schisandra chinensis* and 5-10 part by weight of extract of *Psidium guajava*.

In a preferred embodiment, the pharmaceutical composition used in the present disclosure further comprises 2-3 part by weight of extract of *Hordeum vulgare*.

In a more preferred embodiment, the pharmaceutical composition used in the present disclosure further comprises active ingredient select from the group consisting of: 2-3 part by weight of extract of *Hordeum vulgare*, 8-10 part by weight of extract of *Morus alba*, 5-10 part by weight of extract of *Camellia sinensis*, 5-10 part by weight of extract of grape seed, 2-3 part by weight of Chromium yeast, 3-5 part by weight of powder of Momordicae sharantia, and the combination of at least one of the aforementioned ingredient.

According to the present disclosure, the extract used herein is manufactured according to the method as disclosed in prior art, for example, according to the method comprising the steps of: extracting dry materials with water or alcohol (e.g. hydrous ethanol) under the extraction temperature between 20-75° C.; after extraction, filtering and sterilizing the crude extract; drying the product and obtaining the extract. However, the method of extraction is not limited hereto.

The method of drying the extraction product is not limited in the present disclosure and can be a method as disclosed in prior art, such as air drying, vacuum drying, spray drying, drum drying, or freeze drying (lyophilization).

In a particular embodiment, the extract of *Schisandra chinensis* is obtained by extracting fresh or dry fruit of *Schisandra chinensis* with water and filtering the extracted solution followed by drying.

In a particular embodiment, the extract of *Psidium guajava* is obtained by extracting dry *Psidium guajava* leaves with water or ethanol, filtrating by pressure, and sterilizing the extracted solution followed by spray drying.

In a particular embodiment, the extract of *Hordeum vulgare* is obtained by extracting the seed of *Hordeum vulgare* (also known as malted barley) with water, precipitating the impurities, filtering with membrane, and drying and grinding the residue to obtain the extract.

In a particular embodiment, the extract of *Morus alba* is obtained by extracting dry leaves of *Morus alba* with water or alcohol (e.g. hydrous ethanol), filtering to remove insoluble substance, and concentrating and drying to obtain the extract.

In a particular embodiment, the extract of *Camellia sinensis* is obtained by extracting the leaves of *Camellia sinensis* with water, filtering to remove insoluble substance, and followed by extracting with alcohol, collecting alcohol extracting solution, and concentrating and drying to obtain the extract.

In a particular embodiment, the extract of grape seed is obtained by extracting the seed of grapes with alcohol, filtering to remove impurities, and drying the extracting solution to obtain the extract.

In a particular embodiment, the chromium yeast is obtained by sterilizing and inactivating dry yeast (*Saccharomyces cerevisiae*) by Pasteurization, and drying to obtain chromium yeast. According to this method, the essential minerals, vitamins, and other micronutrients are preserved therein.

In a particular embodiment, the powder of Momordicae sharantia is obtained by slicing and drying the fruit of Momordicae sharantia (also known as bitter melon), followed by grinding.

The ingredients prepared according to the methods above are mixed according to present disclosure to obtain the preparations below for experimentations (Table 1).

TABLE 1

| Ingredient | Preparation 1 | Preparation 2 | Preparation 3 |
|---|---|---|---|
| *Schisandra chinensis* (1-2) | 1 | 2 | 1 |
| *Psidium guajava* (5-10) | 5 | 8 | 5 |
| *Hordeum vulgare* (2-3) | | 3 | 3 |
| *Morus alba* (8-10) | | | 10 |
| *Camellia sinensis* (5-10) | | | 10 |

TABLE 1-continued

| Ingredient | Preparation 1 | Preparation 2 | Preparation 3 |
|---|---|---|---|
| Grape seed (5-10) | | | 10 |
| chromium yeast (2-3) | | | 3 |
| *Momordicae sharantia* (3-5) | | | 5 |

Example 1 Inhibition of Xanthine Oxidase

Xanthine oxidase (XO) is an essential enzyme of human to synthesize uric acid. Purine is metabolized to hypoxanthine, and hypoxanthine is further metabolized to xanthine by XO, and further uric acid is synthesized. Hence, the inhibition of activity of XO would effectively cause the inhibition of synthesis of uric acid. Allopurinol is a common XO inhibitor which is used in medical treatment of high uric acid.

Preparation 1 in the present disclosure was used in the present example (i.e. the composition comprising 1 part by weight of extract of *Schisandra chinensis* and 5 part by weight of extract of *Psidium guajava*).

The inhibition of the preparation 1 according to the present disclosure on the synthesis of uric acid was test on an in vitro analysis platform by xanthine oxidase inhibition assay. In vitro test of XO activity comprised the following steps:

(1) Preparation 1, Phosphate buffer, and XO solution is disposed under 25° C. for 15 minutes for preparing reaction;

(2) Xanthine solution is added as substrate and the mixture is disposed under 25° C. for 15 minutes for reaction;

(3) 1N HCl is added to attenuate the reaction; and (4) The uric acid concentration in the reaction buffer is measured by HPLC. (C18 column, flow rate: 1 ml/min; wavelength: 295 nm)

The result of the present example is shown in FIG. 1. As shown in FIG. 1, 78% of the XO activity was inhibited by the preparation 1 of the present disclosure compared to negative control. The inhibition rate was approximately 94% of the positive control group treated with Allopurinol.

Accordingly, in view of the present example, the composition according to the present disclosure is capable to inhibit the activity of XO, implying the ability to inhibit synthesis of uric acid. Thus the composition can be used in treating the disease or conditions related to high uric acid.

Example 2 Reduction of Blood Uric Acid

Preparation 2 in the present disclosure was used in the present example (i.e. the composition comprising 2 part by weight of extract of *Schisandra chinensis,* 8 part by weight of extract of *Psidium guajava,* and 3 part by weight of extract of *Hordeum vulgare.*

The preparation 2 was administered to the patient suffered from hyperuricemia, wherein the dose is 3 g per patient. The concentration of blood uric acid was measured before administration, 1 hour post administration, and 2 hours post administration. The blood uric acid is detected by uric acid monitoring device: MultiSure (APEXBIO, Taiwan). The result is shown in Table 2.

| Subject | Age | Time | Dose | Uric acid conc.(mg/dL) | Reduction of uric acid (mg/dL) | Reduction of uric acid (%) | Note |
|---|---|---|---|---|---|---|---|
| TH | 70 | 11:00 | 0 | 9.0 | — | — | Fasting |
|  |  | 13:00 | 3 g | 11.9 | — | — | Administering preparation 2, 1 hour (h) after lunch |
|  |  | 14:00 | 0 | 10.2 | 1.70 | 14.29 | 1 h after administering preparation 2 |
|  |  | 15:00 | 0 | 10.2 | 1.7 | 14.29 | 2 h after administering preparation 2 |
| YG | 45 | 11:00 | — | 7.6 | — | — | Fasting |
|  |  | 13:00 | — | 7.9 | — | — | Administering preparation 2, 1 h after lunch |
|  |  | 14:00 | 3 g | 7.8 | 0.10 | 1.27 | 1 h after administering preparation 2 |
|  |  | 15:00 | — | 7.0 | 0.9 | 11.39 | 2 h after administering preparation 2 |
| VC | 38 | 11:00 | — | 8.0 | — | — | Fasting |
|  |  | 13:00 | — | 8.9 | — | — | Administering preparation 2, 1 h after lunch |
|  |  | 14:00 | 3 g | 7.6 | 1.30 | 14.61 | 1 h after administering preparation 2 |
|  |  | 15:00 | — | 6.5 | 2.4 | 26.97 | 2 h after administering preparation 2 |
| WC | 38 | 11:00 | — | 7.4 | — | — | Fasting |
|  |  | 13:00 | — | 7.9 | — | — | Administering preparation 2, 1 h after lunch |
|  |  | 14:00 | 3 g | 6.6 | 1.30 | 16.46 | 1 h after administering preparation 2 |
|  |  | 15:00 | — | 6.3 | 1.6 | 20.25 | 2 h after administering preparation 2 |
| HY | 28 | 11:00 | — | 6.4 | — | — | Fasting |
|  |  | 13:00 | — | 7.3 | — | — | Administering preparation 2, 1 h after lunch |
|  |  | 14:00 | 3 g | 6.2 | 1.10 | 15.07 | 1 h after administering preparation 2 |
|  |  | 15:00 | — | 6.1 | 1.2 | 16.44 | 2 h after administering preparation 2 |

The result of the present example is shown in Table 2. According to table 2, at 1 hour after the patient of hyperuricemia is treated with preparation 2, the level of uric acid reduced 1.27-16.46%; at 2 hour after the patient of hyperuricemia is treated with preparation 2, the level of uric acid reduced 11.39-26.97%.

According, in view of present example, the composition according to the present disclosure can effectively reduce the concentration of uric acid and can be used in the treatment of the disease related to high uric acid.

Example 3 Reduction of Blood Uric Acid

Preparation 3 in the present disclosure was used in the present example (i.e. the composition comprising 1 part by weight of extract of Schisandra chinensis, 5 part by weight of extract of Psidium guajava, 3 part by weight of extract of Hordeum vulgare, 10 part by weight of extract of Morus alba, 10 part by weight of extract of Camellia sinensis, 10 part by weight of extract of grape seed, 3 part by weight of Chromium yeast, and 5 part by weight of powder of Momordicae sharanti).

Human subject (Male: 5; Female: 2) was treated with the preparation 3 as disclosed herein and the level of uric acid was measured. The subject was randomly divided into 2 groups, which as negative control group (placebo) and experiment group.

In order to induce the symptoms of high uric acid, the subject in the experiment group respectively took a high purine diet comprising 330 ml beer and 30 g dry anchovies (223 Kcal in sum). The preparation 3 was administered to the subjects at 20 minutes before inducing high uric acid symptoms, wherein the dose is 3 g (dry weight) per subject, and the level of blood uric acid was measure at 0, 1, 2, 3 hours after taking high purine diet.

All the experiment result was analyzed by SPSS 18.0, including one-way ANOVA followed by Duncan's new multiple range test (DMRT). All the statistic values are presented as average±SD.

Figure 2:
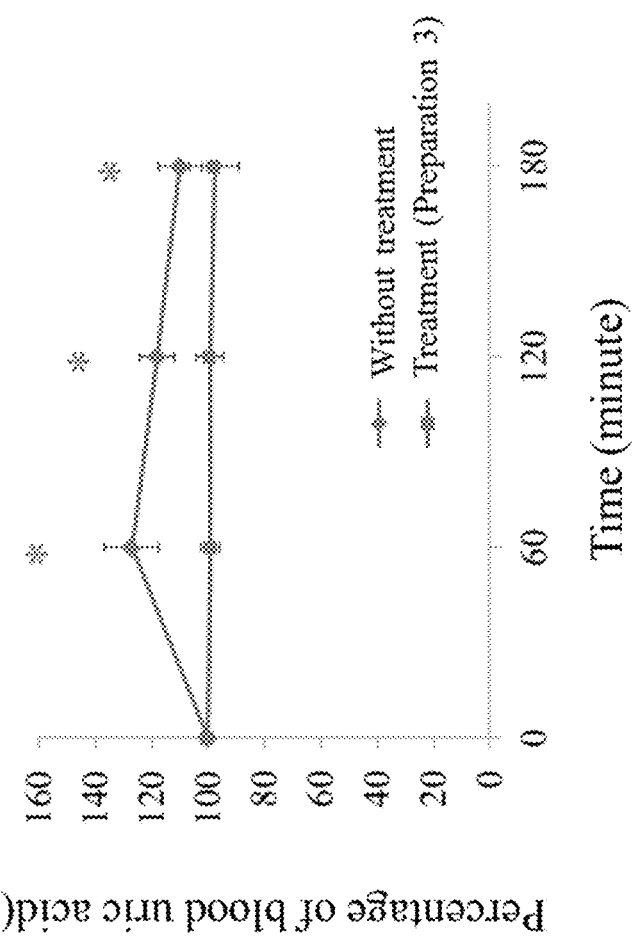
FIG. 2 shows the illustrative result of the reduction of blood uric acid by the pharmaceutical composition according to the present disclosure; wherein the trial subject was treated with the composition according to the present disclosure 20 minutes prior to the induction of hyperuricemia, and blood uric acid concentrations was measured 0, 1, 2, and 3 hours after intake of high purine diet. ($p<0.05$)

According to FIG. 2, the level of blood uric acid in the subjects of the group which was not administered with the preparation 3 (control group) obviously increased, wherein the level approximately increased 31%, 21%, and 10% at 1, 2, 3 hours after taking high purine diet. In contrast, the level of uric acid in the subjects of the group which was administered with the preparation 3 (experimental group) did not increase.

Hence, in view of the present example, the pharmaceutical composition as disclosed herein can prevent the increase of uric acid from high purine diet and can effectively reduce the level of blood uric acid. The pharmaceutical composition can be used in the treatment of the disease related to high uric acid.

Example 4 Protection of Renal Function

Diabetic nephropathy is one of the common complications of diabetes which is caused by the loss of control of blood sugar. Urea would accumulate in body in the condition of dysfunction of kidney, which lead to uremia when the dysfunction is severe.

In the present example, the diabetic rats was treated with the composition of preparation 3 and the improvement of diabetic symptoms was observed.

Firstly, 40 male Sprague-Dawley rats (6-week-old) were randomly assign to five groups (8 rats for each group) including: diabetic control group (DM), normal control group (N), and the experiment groups which were respectively administered with 1×, 2×, 5× dose of preparation 3. Each group of rats were reared in cage under the condition of controlled temperature (22±2° C.) and humidity (55±5%) and 12 hours of day light cycle.

Rats were fed with high fat (>20%) and high refined sugar (sucrose, or the composition of sucrose and fructose>50%) diet together with low dose of nicotinamide (NA)(Sigma, USA) and Streptozotocin(STZ)(Sigma, USA), in order to induce the diabetic-like and hyperglycemia symptoms. In the duration from the first day of experiment to the eighth week before sacrifice, the rats were continuously fed with the diet as described above to induce the occurring of hyperglycemia. Also in the abovementioned experiment, the rats were injected intraperitoneally with NA (30~60 mg/kg) every 3 days and then were injected with STZ(10~20 mg/kg) 15-30 minutes later, until the diabetic symptoms were successfully induced.

The estimation of dose of composition of preparation 3 is in accordance with "Estimating the maximum safe starting dose in initial clinical trials for therapeutics in adult healthy volunteers" (54-1) published by USFDA, with a standard of 60 kg adult. As for higher experiment organism, the dose is in principle in accordance with the conversion that the 6.2 time of dose of estimated intake amount of human subject (mg/kg/day) corresponds to 1 time of dose of rats.

In the late stage of diabetic nephropathy, the function of kidney to filter gradually impairs that the kidney is incapable to filtrate and excrete urea. In the present example, each of the rats of the groups were daily administered with the composition of preparation 3 according to the followings: the rats of normal control group were orally fed with common feed (MFG) in 1 mL deionized $H_2O$ by gavage; the rats of diabetic control group (DM) were orally fed with high fat diet (HFD) in 1 mL deionized $H_2O$ by gavage; the rats of 1× dose group (1×) were orally fed with the composition of the preparation 3 (283 mg/kg) and high fat diet (HFD) by gavage; and the rats of 2× and 5× dose group (2× and 5×) were respectively fed with the composition of the preparation 3 as the 1× group except that the doses were 566 mg/kg and 1416 mg/kg. During the 8 weeks of experimentation, the variation of the blood urea of the rats was monitored and the effect of administration of the composition was analyzed.

Figure 3:
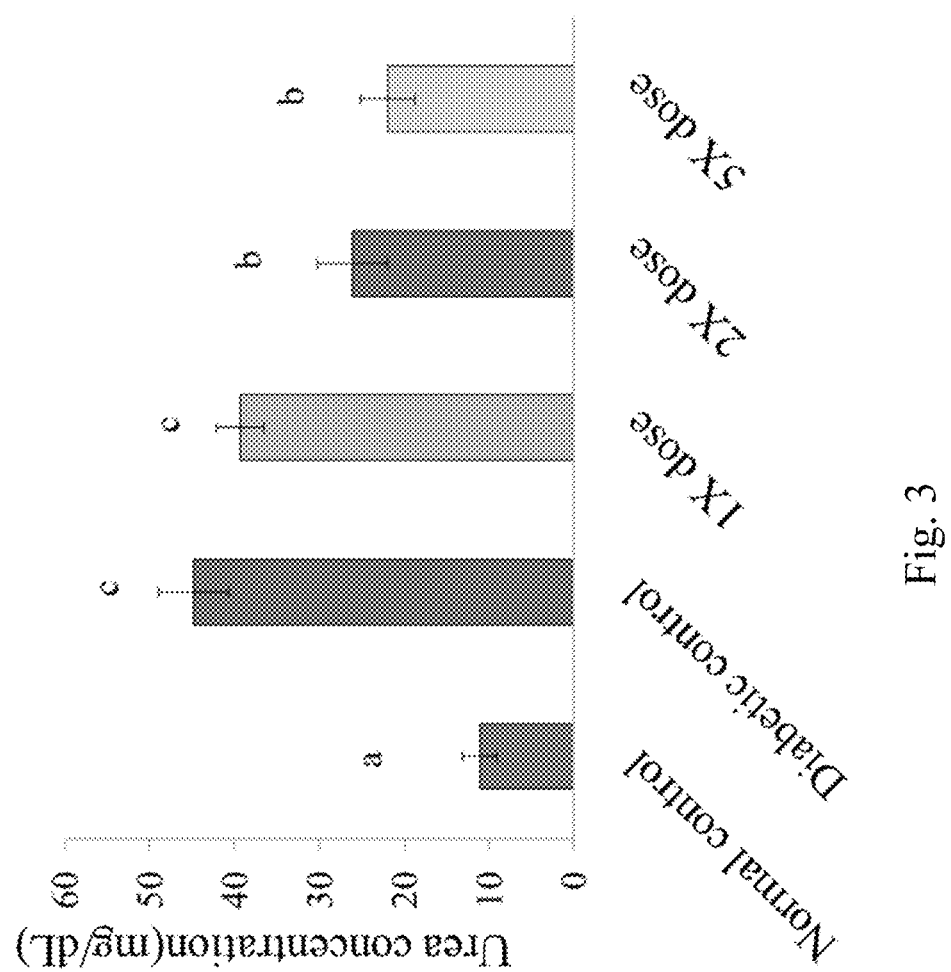
FIG. 3 shows the illustrative result of the reduction of blood urea of rat by the composition according to the present disclosure; wherein the diabetic rats was treated with the composition according to the present disclosure (1×, 2×, or 5× dose) for 8 weeks and then the concentration of blood urea of rats was measured. ($p<0.05$)

FIG. 3 shows the result of the present example. According to FIG. 3, the concentration of blood urea of the rats in the groups treated with the composition of preparation 3 in a dose of 2× and 5× is significantly lower than the rats in the diabetic group(DM), which is not treated. (p<0.05) Further, if merely 1× dose was administered, the concentration of blood urea has a tendency of reducing however the reduction is not significant than the diabetic group (DM). (p>0.05) Thus, in view of the present example, the composition as disclosed herein can effectively reduce the concentration of blood urea and protect the function of kidney as well as prevent diabetic nephropathy.

Example 5 Protection of Pancreatic Cell

In the present embodiment, the rats, the condition of rearing, and the composition (preparation 3) employed herein are the same as those in example 4, which is not repeated herein.

The method of homeostatic model assessment of insulin resistance (HOMA-IR) is utilized herein as an index of insulin sensitivity. The resistance of insulin is determined according to HOMA-IR.

The blood of fasting rats was collected regularly during the experiment and the concentration of insulin and glucose in blood under fasting were measured. The measure of insulin under fasting is conducted with Rat Insulin ELISA Kit (Mercodia, USA). The measure of glucose under fasting comprised: collecting the blood of rat via tail vein every week and analyzing the concentration by a glucose detector (Optium xceed), which has a detectible sensitivity for glucose concentration between 20-500 mg/dL. The formula for calculating HOMA-IR is:

HOMA-IR index=(glucose concentration in serum under fasting (mmol/L)×insulin concentration in serum under fasting (μU/mL))/22.5

Figure 4:
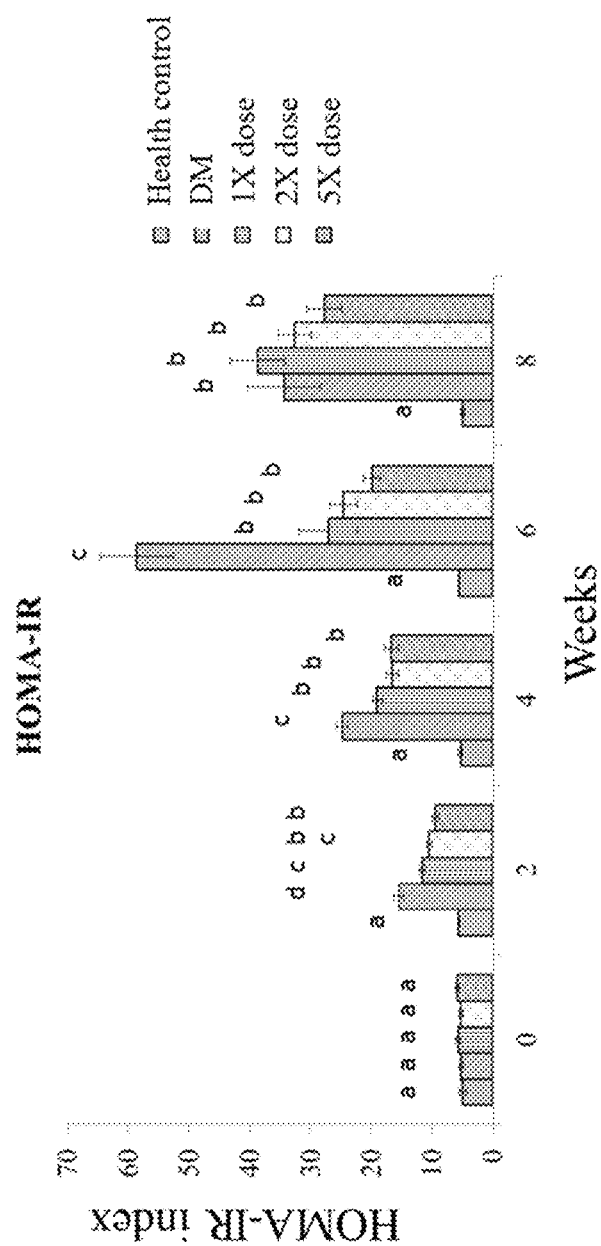
FIG. 4 shows the illustrative result of the reduction of HOMA-IR index by the composition according to the present disclosure; wherein the diabetic rats was treated with the composition according to the present disclosure (1×, 2×, or 5× dose) for 8 weeks and then the insulin resistance of the rats was measured and HOMA-IR was calculated. ($p<0.05$)

The result of analysis of HOMA-IR index is shown in FIG. 4. In week 0, the HOMA-IR index of each group did not change. However, since week 2, the HOMA-IR indexes of the groups treated with the composition of preparation 3 (1×, 2×, and 5×) were significantly lower than that of the diabetic group (DM)(P<0.05). During week 4 to 6, the HOMA-IR indexes of the groups treated with the composition of preparation 3 (1×, 2×, and 5×) were slightly higher, compared to that in week 2 but were still significantly lower than that of the diabetic group (DM)(P<0.05).

In addition, in week 8, as the concentration of glucose increased, the concentration of glucose of diabetic group (DM) was higher than that of normal group (P<0.05) and however there was not significant difference between the diabetic group and the experiment groups (1×, 2×, and 5× dose). It implied that it was because the rats of the diabetic groups had acquired a severe insulin resistance and the pancreatic β cell was dysfunctional due to exhaustion, being unable to secret insulin in response to glucose concentration. Thus, in view of FIG. 4, the administration of the composition of preparation 3 can effectively maintain the normal function of pancreatic β cell to secret insulin and maintain the insulin sensitivity of diabetic rats.

Further, the rats were sacrificed in week 8 and the pancreatic tissue were subject to hematoxylin and eosin (HE) stain and immunohistochemistry (IHC) to observe the morphology of the pancreatic cell of each groups of rats and weigh the β cells. The measure of β cell is according to the method disclosed in prior art (Saisho et al., 2013), comprising: sectioning a piece from pancreas for calculation the mass of β cells, selecting several region for calculation, and dividing the mass by the total weight of tissue to show a percentage, with the deviation being calibrated. The formula for calculating the mass of β cells is:

Mass of βcells=the total weight of pancreas tissue× [(number of βcells/sum of cell number in pancreas)/area of pancreatic cells]

Figure 5:
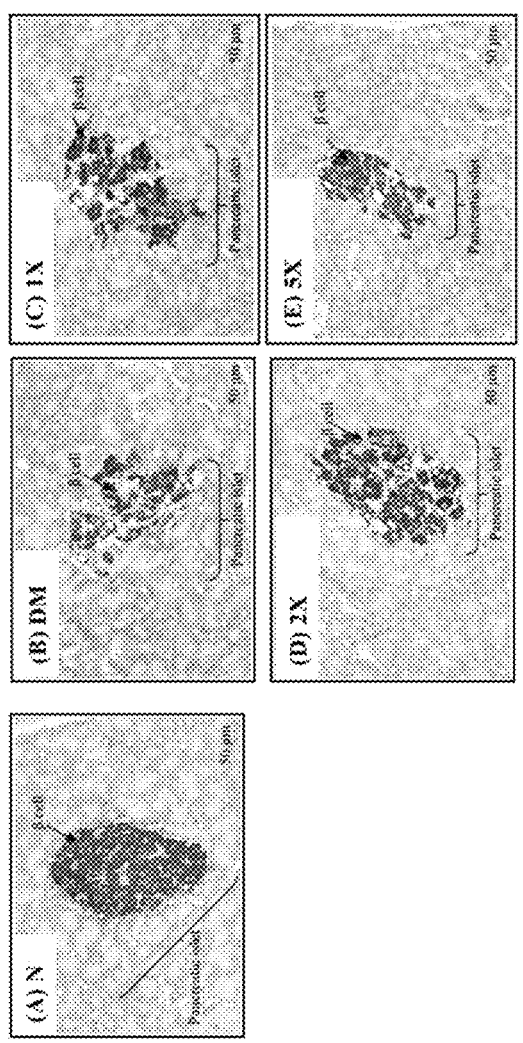
FIG. 5 shows the illustrative result of the protection of pancreatic cells by the composition according to the present disclosure; wherein the diabetic rats were treated with the composition according to the present disclosure for 8 weeks and then the pancreas of rat is subject to sectioning and IHC staining. The morphology of β cells of the different groups are shown. ((A) N: normal control; (B) DM: diabetic mellitus control; (C) 1×, (D) 2×, or (E) 5× dose) (p<0.05)

FIG. 5 shows the difference on the morphology of the pancreas cells of the groups of rats. FIG. 5 discloses that the amount of β cells of the diabetic rats (DM group) was obviously less than the rats in other groups and the morphological appearance was partial, which implied that the diabetic rats has impaired renal function. In contrast, it was observed that the rats of the groups treated with 1×, 2×, or 5× dose of the composition had a pancreas tissue which has more and intact β cells.

Figure 6:
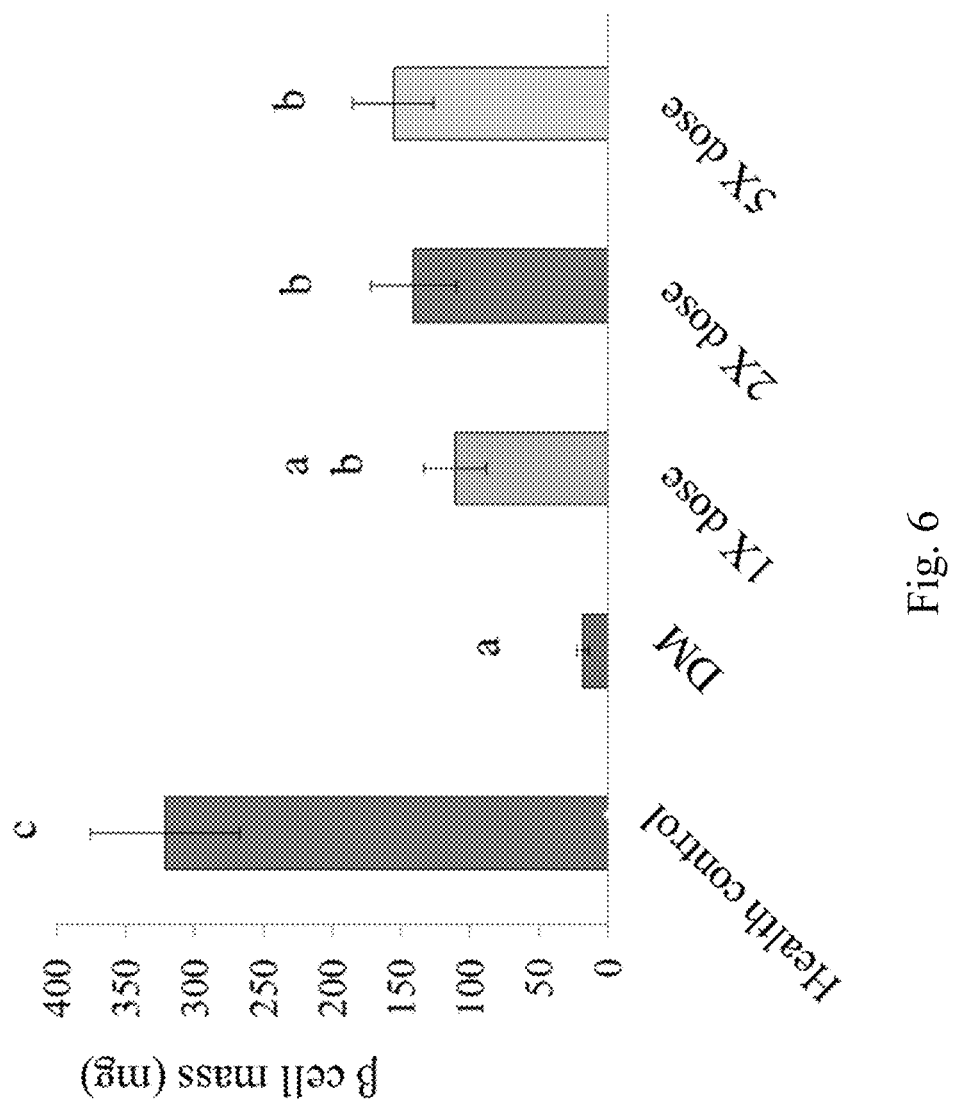
FIG. 6 shows the illustrative result of the weight of β cells of the groups according to FIG. 5.

Further according to FIG. 6, the β cell mass of the rats of the groups treated with 1×, 2×, or 5× dose of the preparation 3 was significantly higher than that of diabetic rats (P<0.05);

the β cell mass of the rats of the groups treated with 2× or 5× dose of the preparation 3 was also higher than that of the rats treated with 1× dose of the preparation. In view of this, the composition of preparation 3 shows a dose-dependent tendency for protection of pancreas cells.

In view of FIGS. 5 and 6, the composition as disclosed herein can effectively maintain the normal function of β cell and also can maintain the mass of pancreatic β cell.

Example 6 Reducing Organ Fat, Body Fat, and Body Weight and Increasing the Ratio of Body Muscle 16 6-week-old male Sprague-Dawley rats were randomly divided into three (3) groups including health control group (n=8), high fat obesity group (n=4), and a 1× dose group (n=4).

In the beginning of experiment, the rats were fed with normal diet (MFG) for 1 week for acclimation. Afterwards, the health control group was still fed with normal diet, and the high fat obesity group was changed to high fat diet to induce obesity, wherein the high fat diet comprised 5.24 kcal/g calories and 60% per 100 Kcal were fat. At the same time, the health control group and the high fat diet obesity group were treated with deionized water yet the 1× dose group was additionally administer with the composition as disclosed herein.

Except for the difference recited above, the rats, the condition of rearing, and the composition (preparation 3) employed in the present example are the same as those in example 4, which is not repeated herein.

After eight (8) weeks of feeding, the rats were sacrificed and the fat of organ and body and body weight were analyzed. The epididymal adipose tissue(EAT), perirenal fat(PF), and mesenteric fat(MF) of the sacrificed rats were weighed and the body fat percentage (BFP) was calculated according to the following formula:

BFP=[Mass of body fat (g)/body weight(g)]×100% wherein mass of body fat (g)=EAT(g)+PF(g)+MF(g)

Figure 7:
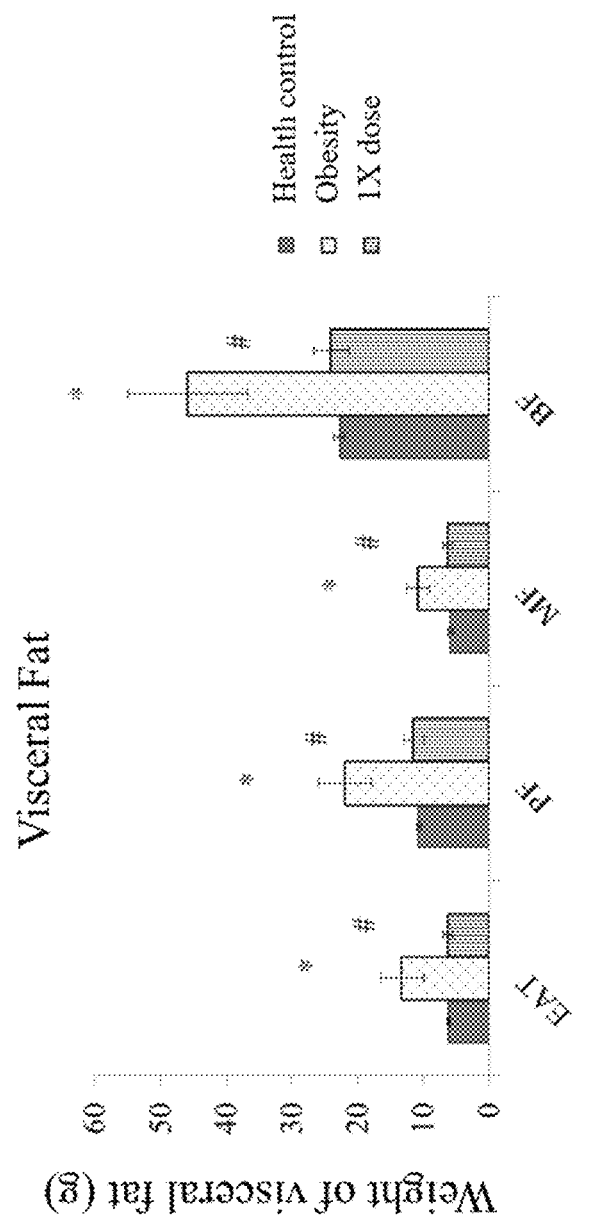
FIG. 7 shows the illustrative result of the effect on weight of visceral fat by the composition according to the present disclosure; wherein the obese rats were treated with the composition according to the present disclosure for 8 weeks and then the weight of visceral fat was measured. (EAT: epididymal adipose tissue, PF: perirenal fat, MF: mesenteric fat, BF: body fat) (p<0.05)

According to FIG. 7, the visceral fat of the rats of high fat obesity group, including EAT, PF, and MF, was significantly 2 times higher than that of the 1× dose group. Hence, in the group treated with preparation 3, the EAT, PF, and MF as well as body fat were not significantly increased and were recovered to the same level as the health control group.

Figure 8:
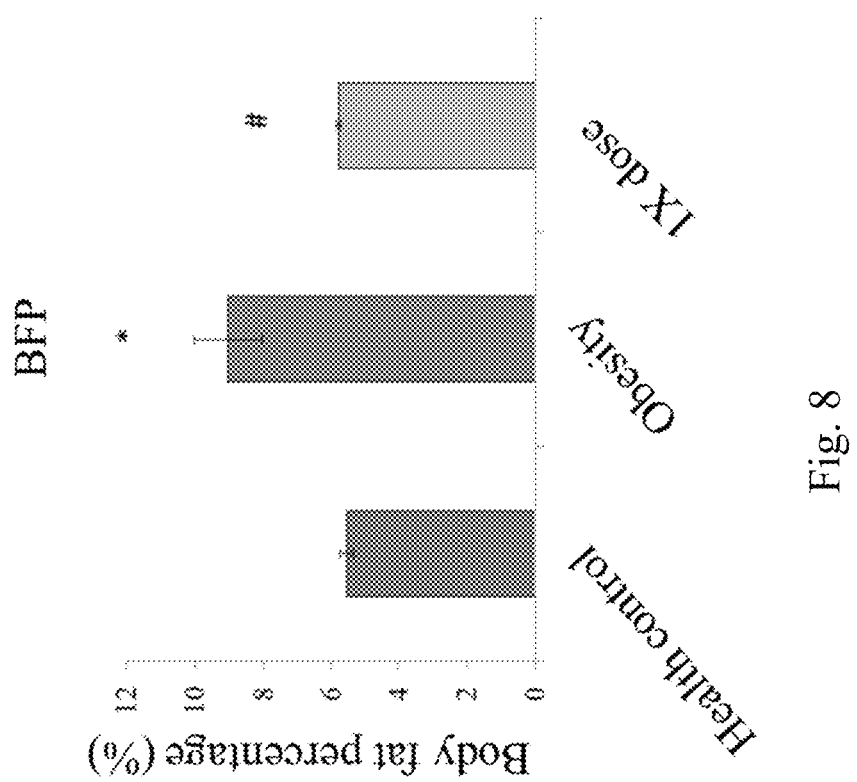
FIG. 8 shows the illustrative result of the effect on the body fat percentage (BFP) of the groups of rats according to FIG. 7 by the composition according to the present disclosure. (p<0.05)

Additionally, according to FIG. 8, the BFP of the rats of high fat diet were 1.5 times higher than that of the health control group, and the BFP of the 1× dose group treated with the composition according to preparation 3 did not significantly increase and was approximately 60% compared to the high fat obesity group, as that of the health control group.

Hence, according to the BFR and the mass of organ fat disclosed in FIG. 7, the administration of the composition according to preparation 3 can effectively inhibit the increase of body fat and organ fat, and maintain the fats in a normal range.

Figure 9:
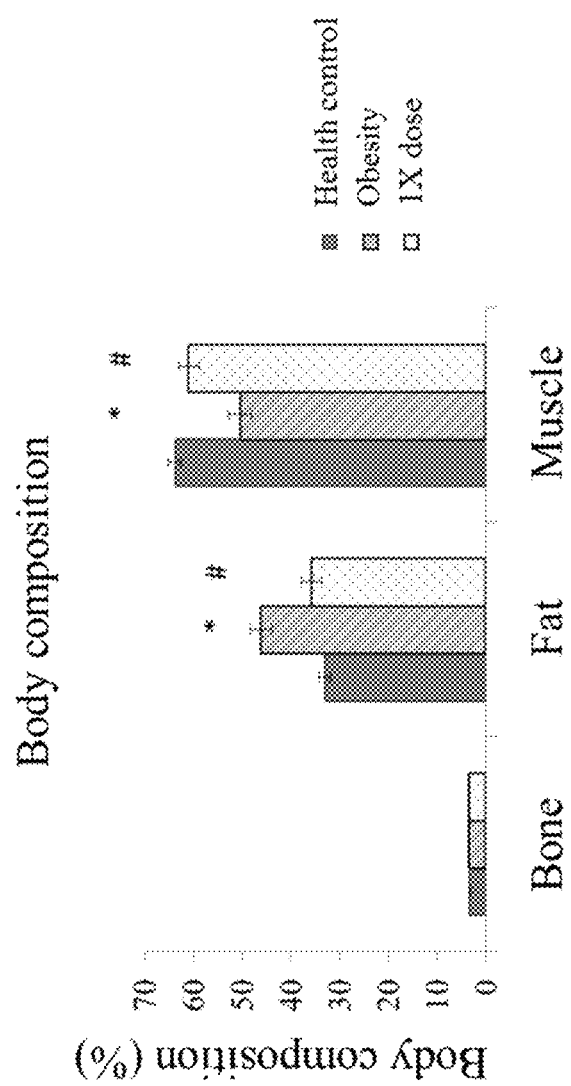
FIG. 9 shows the illustrative result of the effect on the body composition by the composition according to the present disclosure; wherein the obese rats were treated with the composition according to the present disclosure for 8 weeks and the ratio of bone, fat, and muscle was evaluated. (p<0.05)

Furthermore, the body compositions of the rats in each group were analyzed by Dual-energy X-ray absorptiometry, the result of which is disclosed in FIG. 9. According to FIG. 9, the BFP of the rats of high fat obesity group was 40% higher than that of the health control group and the 1× dose group, and the ratio of body muscle was significantly reduced to 80% compared to that of the health control group and the 1× dose group.

On the contrary, the BFP and the ratio of body muscle of the rats of the group treated with 1× dose of preparation 3 were similar to that of the health control group.

Figure 10:
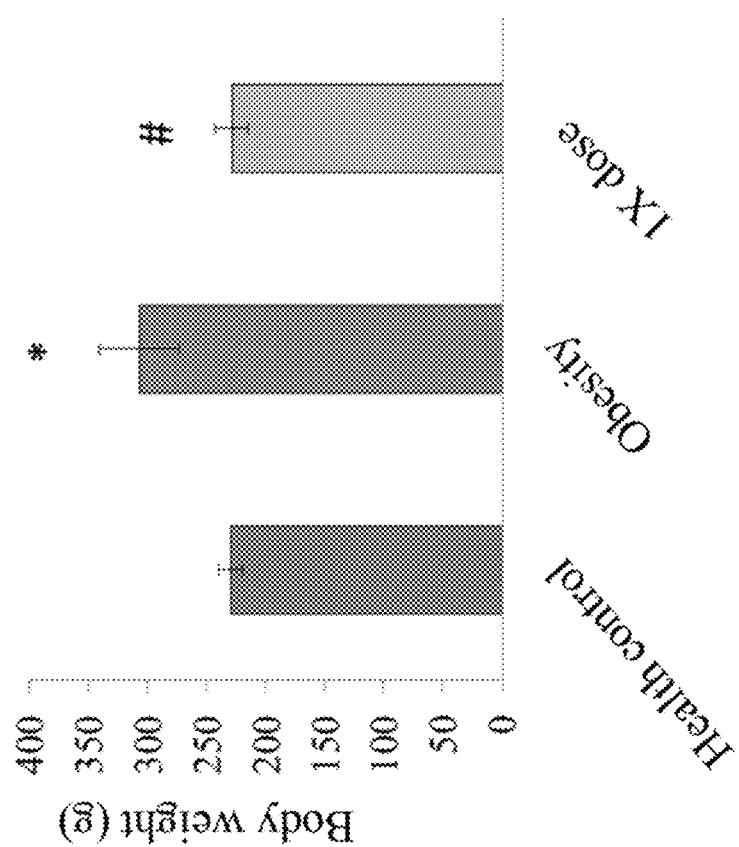
FIG. 10 shows the illustrative result of the effect on body weight by the composition according to the present disclosure; wherein the obese rats were treated with the composition according to the present disclosure for 8 weeks and the body weight was measured. (p<0.05)

Additionally, FIG. 10 discloses the change of body weight of the rats of each group. The body weight of the rats of high fat obesity group was significantly 34% higher than that of the health control group and the 1× dose group, indicating that the composition according to preparation 3 can effectively maintain body weight and prevent obesity.

Figure 11:
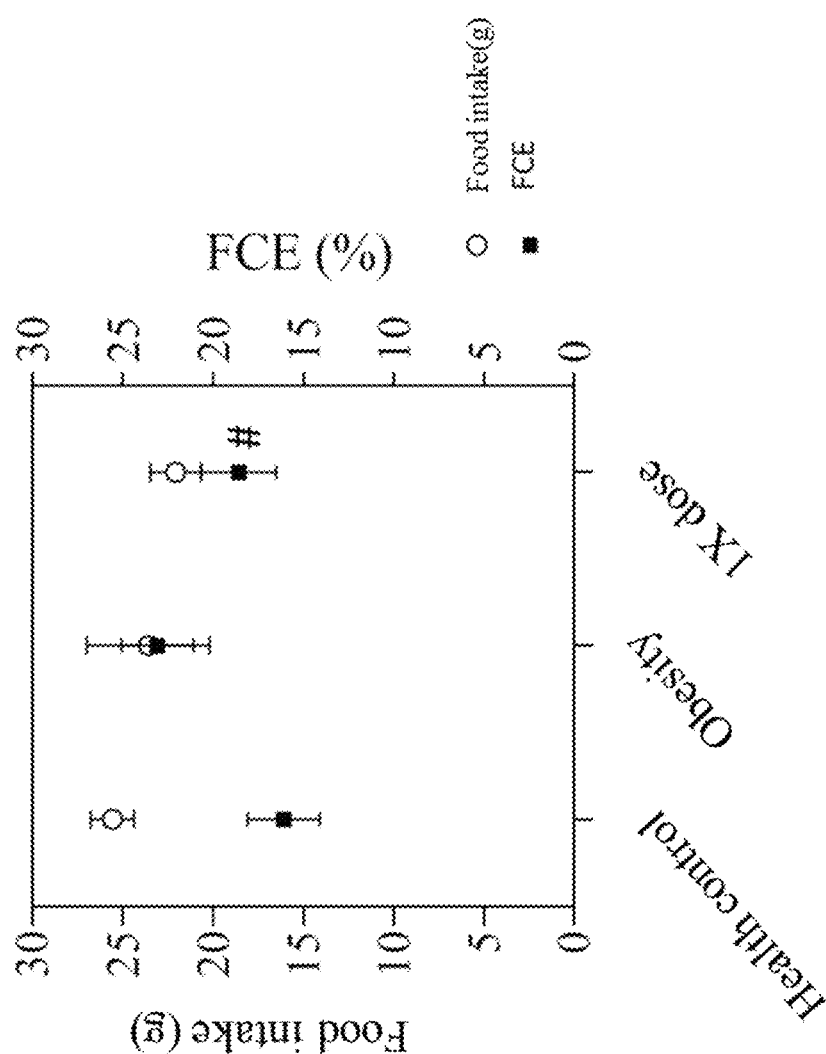
FIG. 11 shows the illustrative result of the effect on food conversion efficiency (FCE) by the composition according to the present disclosure; wherein the obese rats were treated with the composition according to the present disclosure for 8 weeks and the FCE was measured. (p<0.05)

The food conversion efficiency (FCE) was calculated according to the intake of food and the change of body weight of the rats of each group. FIG. 11 discloses the result of calculation of FCE. The amount of intake of food was similar for the rats of 1× dose group and the rats of high fat obesity group, but the FCE of the 1× dose group was 5% lower than that of the high fat obesity group. Thus it is shown that the composition according to preparation 3 can effectively reduce FCE.

In view of FIG. 7 to FIG. 10, the composition according to the present disclosure can effectively reduce body fat and organ fat, reduce body weight and body fat, and effectively increase the ratio of body muscle. Further in view of FIG. 11, the composition according to the present disclosure can also reduce food conversion efficiency and further reduce body weight.

While preferred embodiments of the present disclosure have been shown and described herein, it will be obvious to those skilled in the art that such embodiments are provided by way of example only and can be implemented in combinations. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

We claim:

1. A method of treating hyperuricemia or gout, comprising administering to a subject in need thereof a therapeutically effective amount of a pharmaceutical composition comprising:
    1-2 parts by weight of an extract of Schisandra chinensis and
    5-10 parts by weight of an extract of *Psidium guajava*,
    wherein the therapeutically effective amount is an amount effective to inhibit xanthine oxidase activity in the subject.

2. The method of claim 1, wherein the pharmaceutical composition comprises 1 part by weight of the extract of Schisandra chinensis and 5 parts by weight of the extract of *Psidium guajava*.

3. The method of claim 1, wherein the pharmaceutical composition further comprises 2-3 parts by weight of an extract of *Hordeum vulgare*.

4. The method of claim 1, wherein the pharmaceutical composition further comprises an active ingredient selected from the group consisting of:
    2-3 parts by weight of an extract of *Hordeum vulgare*,
    8-10 parts by weight of an extract of *Morus alba*,
    5-10 parts by weight of an extract of *Camellia sinensis*,
    5-10 parts by weight of an extract of grape seed,
    2-3 parts by weight of chromium yeast,
    3-5 parts by weight of a powder of *Momordicae charantia*,
    and a combination thereof.

5. The method of claim 1, wherein the pharmaceutical composition further comprises an active ingredient selected from the group consisting of:

5-10 parts by weight of an extract of *Camellia sinensis,*
5-10 parts by weight of an extract of grape seed,
and a combination thereof.

\* \* \* \* \*